(12) United States Patent
Ide et al.

(10) Patent No.: US 8,983,890 B2
(45) Date of Patent: Mar. 17, 2015

(54) CALCULATING RISK ASSESSMENT VALUE OF EVENT SEQUENCE

(71) Applicant: International Business Machines Corporation, Armonk, NY (US)

(72) Inventors: Tsuyoshi Ide, Kanagawa (JP); Raymond H. Rudy, Tokyo (JP)

(73) Assignee: International Business Machines Corporation, Armonk, NY (US)

( * ) Notice: Subject to any disclaimer, the term of this patent is extended or adjusted under 35 U.S.C. 154(b) by 290 days.

(21) Appl. No.: 13/681,688

(22) Filed: Nov. 20, 2012

(65) Prior Publication Data

US 2013/0144824 A1 Jun. 6, 2013

(30) Foreign Application Priority Data

Dec. 5, 2011 (JP) ................................. 2011-266154

(51) Int. Cl.
*G06N 5/02* (2006.01)
*G06Q 50/22* (2012.01)
*G06Q 10/06* (2012.01)

(52) U.S. Cl.
CPC .............. *G06N 5/02* (2013.01); *G06Q 10/0635* (2013.01); *G06Q 50/22* (2013.01)
USPC ......................................................... 706/46

(58) Field of Classification Search
USPC ......................................................... 706/46
See application file for complete search history.

(56) References Cited

U.S. PATENT DOCUMENTS

| | | | | |
|---|---|---|---|---|
| 7,849,124 B2* | 12/2010 | Ide | ................................ | 708/422 |
| 8,138,974 B2* | 3/2012 | Hido et al. | .................... | 342/417 |
| 8,345,170 B2* | 1/2013 | Iwata et al. | .................... | 348/730 |
| 8,405,551 B2* | 3/2013 | Hido et al. | .................... | 342/451 |
| 8,595,155 B2* | 11/2013 | Ide | .................................. | 706/12 |
| 8,600,721 B2* | 12/2013 | Ide et al. | .......................... | 703/13 |
| 8,640,015 B2* | 1/2014 | Ide et al. | ........................ | 714/799 |
| 8,682,633 B2* | 3/2014 | Ide et al. | .......................... | 703/13 |
| 8,747,275 B2* | 6/2014 | Shioiri et al. | ................. | 475/220 |

FOREIGN PATENT DOCUMENTS

JP 2009237914 A 10/2009

OTHER PUBLICATIONS

Anomaly Detection on Collective Moving Patterns: Manifold Learning Based Analysis of Traffic Streams, Su Yang ; Wenbin Zhou Privacy, Security, Risk and Trust (PASSAT) and 2011 IEEE Third Intl Conference on Social Computing (SocialCom), on DOI: 10.1109/PASSAT/SocialCom.2011.10.*

(Continued)

*Primary Examiner* — Michael B Holmes
(74) *Attorney, Agent, or Firm* — Cantor Colburn LLP

(57) ABSTRACT

Provided are a method, an apparatus and a computer program for calculating a risk assessment value for an event sequence, which are capable of calculating the risk assessment value of each even sequence by calculating a totally ordered set on the basis of a partially ordered set indicating the event sequence. The risk assessment value of an event sequence that is a partially ordered set indicating some events of an event group of M kinds of events (M is a finite natural number) in a time series. The partially ordered set is converted into an approximate totally ordered set, and an M-dimensional feature vector is calculated based on the totally ordered set obtained by the conversion. A projection matrix for calculating the risk assessment value is calculated using the calculated M-dimensional feature vector.

4 Claims, 7 Drawing Sheets

(56) References Cited

OTHER PUBLICATIONS

Investigation of the influence of series compensation in AC transmission systems on bus connected parallel generating units with respect to subsynchronous resonance (SSR) Kumar, R. ; Harada, A. ; Merkle, M. ; Miri, A.M. Power Tech Conference Proceedings, 2003 IEEE Bologna Volume: 3 DOI: 10.1109/PTC.2003.1304525 Publication Year: 2003.*

Assessment of HVDC grid segmentation for reducing the risk of cascading outages and blackouts Mousavi, O.A. ; Bizumic, L. ; Cherkaoui, R. Bulk Power System Dynamics and Control—IX Optimization, Security and Control of the Emerging Power Grid (IREP), 2013 IREP Symposium DOI: 10.1109/IREP.2013.6629372 Publication Year: 2013 , pp. 1-10.*

Predicted reliability of aerospace electronics: Application of two advanced probabilistic concepts Suhir, E. Aerospace Conference, 2013 IEEE DOI: 10.1109/AERO.2013.6496824 Publication Year: 2013 , pp. 1-13.*

* cited by examiner

Figure 3

| NAME OF EVENT SEQUENCE | LIST OF EVENTS | LABEL VALUE |
|---|---|---|
| EVENT SEQUENCE 1 : | A B C E F | 1.0 |
| ... | ... | ... |
| EVENT SEQUENCE i : | B A C E F | 1.0 |
| EVENT SEQUENCE j : | D E F G B | 0.0 |
| ... | ... | ... |

Figure 4

$$S_{ij} = \begin{pmatrix} 1 & 0.1 & 0.3 & 0.9 \\ \cdots & 1 & 0.5 & \cdots \\ \cdots & \cdots & 1 & 0 \\ \cdots & \cdots & \cdots & 1 \end{pmatrix} \begin{matrix} A \\ B \\ C \\ D \end{matrix}$$

$$\begin{matrix} A & B & C & D \end{matrix}$$

Figure 5

$$X^{(1)} = \begin{pmatrix} 0 & \beta & \beta^2 & 0 & \beta^3 & \beta^4 & 0 \\ 0 & 0 & \beta & 0 & \beta^2 & \beta^3 & 0 \\ 0 & 0 & 0 & 0 & \beta & \beta^2 & 0 \\ 0 & 0 & 0 & 0 & 0 & 0 & 0 \\ 0 & 0 & 0 & 0 & 0 & \beta & 0 \\ 0 & 0 & 0 & 0 & 0 & 0 & 0 \\ 0 & 0 & 0 & 0 & 0 & 0 & 0 \end{pmatrix} \begin{matrix} A \\ B \\ C \\ D \\ E \\ F \\ G \end{matrix}$$

$$\begin{matrix} A & B & C & D & E & F & G \end{matrix}$$

CALCULATING RISK ASSESSMENT VALUE OF EVENT SEQUENCE

PRIORITY

This application claims priority to Japanese Patent Application No. 2011-266154, filed Dec. 5, 2011, and all the benefits accruing therefrom under 35 U.S.C. §119, the contents of which in its entirety are herein incorporated by reference.

BACKGROUND

The present invention relates to a method, an apparatus, and a computer program for calculating a risk assessment value of an event sequence, with which a risk assessment value indicating a risk of the occurrence of a predetermined incident is calculated for each sequence of some of events that occur in a time series.

It is often considered that a large number of events occur in a time series as omens of a critical incident before the occurrence of the critical incident. Hence, it is preferable to estimate the possibility that a critical incident will occur based on a group of events (hereinafter referred to as "an event sequence") that occur in a time series, and to issue a warning in advance.

However, it is often unclear which event sequence is linked to the occurrence of what critical incident. In addition, it is difficult to list all the possible cases in advance, and the number of event sequences considered to occur is often huge. Under these circumstances, there have been developed many systems for predicting what incident will possibly occur by using a method such as modeling with a neuron model or the like, or estimating a risk assessment value.

Japanese Patent Application Publication No. 2009-237914, for example, discloses a risk prediction device with which risk prediction for a case including both a majority class and a minority class can be made according to actual instances on the basis of their scores calculated in consideration of their attributes. In JP2009-237914, an attribute highly related to a risk factor can be accurately identified even from imbalanced training data in which the number of instances in the majority class is much larger than that of the minority class.

SUMMARY

In one embodiment, a method of determining a risk assessment value of an event sequence which is a partially ordered set indicating some events of an event group of M kinds of events in a time series, wherein M is a finite natural number, includes converting, with a processing device, the partially ordered set into an approximate totally ordered set; calculating an M-dimensional feature vector from the totally ordered set obtained by the conversion; and calculating a projection matrix for calculating the risk assessment value on the basis of the calculated M-dimensional feature vector.

In another embodiment, a method of determining a risk assessment value of an event sequence which is a partially ordered set indicating some events of an event group of M kinds of events in a time series, wherein M is a finite natural number, includes converting, with a processing device, the partially ordered set into an approximate totally ordered set; and on the basis of the totally ordered set obtained by the conversion, calculating a positive semi-definite matrix that minimizes a calculation error of a label value indicating whether or not a risk occurs, and calculating a projection matrix for calculating the risk assessment value on the basis of the calculated positive semi-definite matrix.

In another embodiment, an apparatus configured to calculate a risk assessment value of an event sequence which is a partially ordered set indicating some events of an event group of M kinds of events in a time series, wherein M is a finite natural number, includes a converter configured to convert the partially ordered set into an approximate totally ordered set; a feature vector calculator configured to calculate an M-dimensional feature vector from the totally ordered set obtained by the conversion; and a projection matrix calculator configured to calculate a projection matrix for calculating the risk assessment value on the basis of the calculated M-dimensional feature vector.

In another embodiment, a computer readable storage medium having computer readable instructions stored thereon that, when executed by a computer, implement a method of determining a risk assessment value of an event sequence which is a partially ordered set indicating some events of an event group of M kinds of events in a time series, wherein M is a finite natural number. The method includes converting, with a processing device, the partially ordered set into an approximate totally ordered set; calculating an M-dimensional feature vector from the totally ordered set obtained by the conversion; and calculating a projection matrix for calculating the risk assessment value on the basis of the calculated M-dimensional feature vector.

BRIEF DESCRIPTION OF THE SEVERAL VIEWS OF THE DRAWINGS

FIG. 3 is an illustration of event sequences acquired by the risk calculator according to the first exemplary embodiment of the present invention.

FIG. 4 is an illustration of a similarity matrix S indicating similarities among events in an event sequence.

FIG. 5 is an illustration of a partially ordered matrix generated by the risk calculator according to the first exemplary embodiment of the present invention.

DETAILED DESCRIPTION

Figure 1:
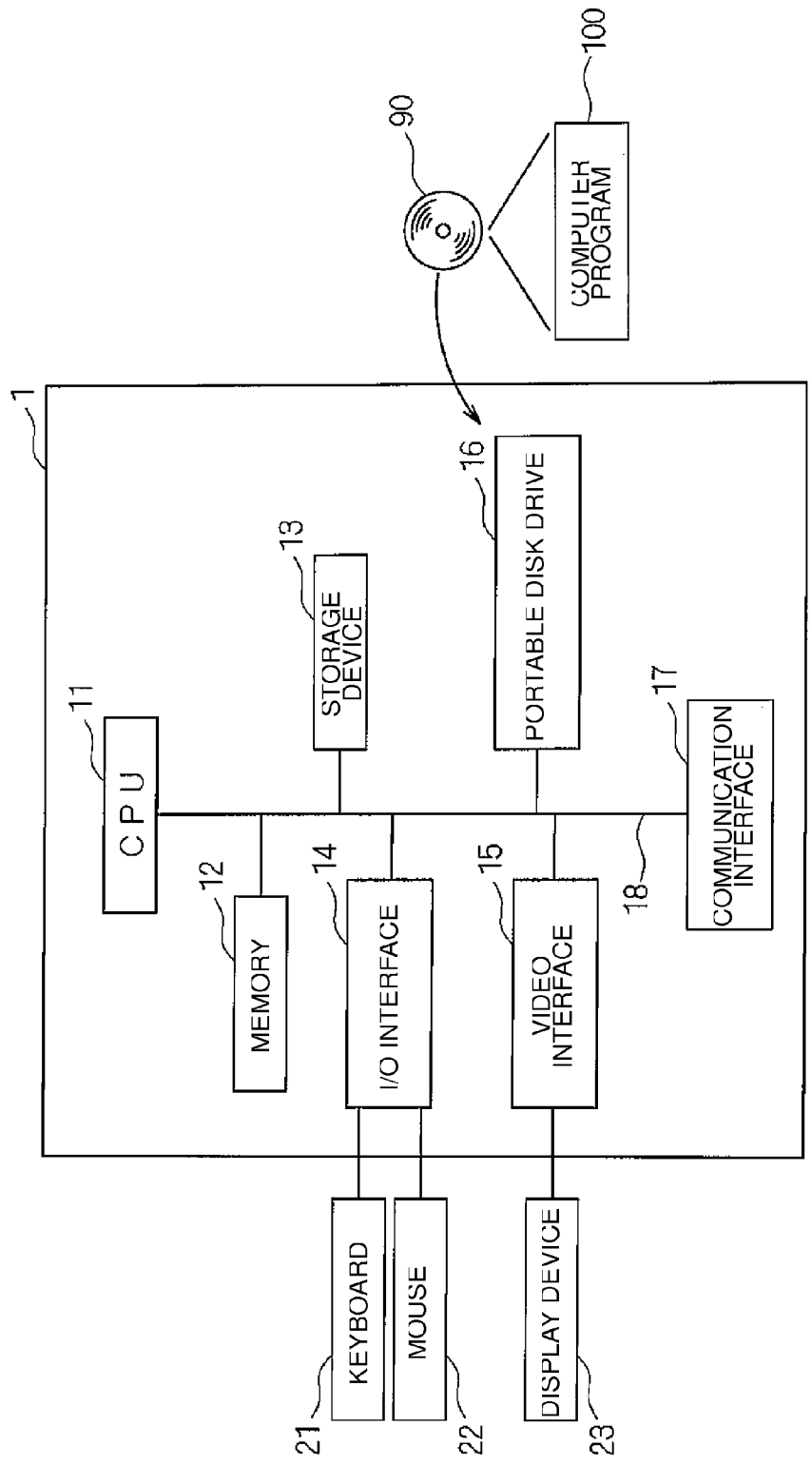
FIG. 1 is a block diagram schematically illustrating a configuration of a risk calculator according to a first exemplary embodiment of the present invention.

With respect to the aforementioned Japanese Patent Application Publication No. 2009-237914, the majority class is not necessarily always identified, and it is quite often that there are a wide variety of attribute items. In addition, even in the case of two sequences of events with the same attribute items, different incidents often finally occur due to a difference in the time series order of the events between the sequences. Thus, there is a problem that it is practically difficult to previously issue a warning that this is an omen of a critical incident, on the basis of the scores simply calculated in consideration of the attributes alone.

In the case of events in the medical field in particular, it is practically impossible to identify all the event sequences linked to a critical incident that may possibly occur. Even if all the event sequences can be identified, the event sequences thus identified are difficult to use as an actual model because the completely same event sequences are considered to be hardly present. In addition, there has been no means for comparing event sequences different in length and elements, and it has been difficult to objectively calculate a risk assessment value on the basis of event sequence.

Accordingly embodiments herein are disclosed in view of the aforementioned circumstances and provide a method, an apparatus, and a computer program for calculating a risk assessment value for an event sequence, which are capable of calculating the risk assessment value for each event sequence by calculating a totally ordered set on the basis of a partially ordered set indicating the event sequence.

A method according to a first invention is a method executable by an apparatus configured to calculate a risk assessment value of an event sequence which is a partially ordered set indicating some events of an event group of M kinds of events (M is a finite natural number) in a time series, the method including the steps of: converting the partially ordered set into an approximate totally ordered set; calculating an M-dimensional feature vector from the totally ordered set obtained by the conversion; and calculating a projection matrix for calculating the risk assessment value on the basis of the calculated M-dimensional feature vector.

In addition, in a method according to a second embodiment, the method of the first invention further includes: generating an M-dimensional spare ordered matrix on the basis of the partially ordered set; and calculating a dense ordered matrix having highest similarity to the generated sparse ordered matrix.

In a method according to a third embodiment, the method of the second embodiment further includes: converting the calculated dense ordered matrix into a column vector; and performing linear regression to calculate a projection matrix for calculating a label value indicating whether or not a risk occurs.

In addition, a method according to a fourth embodiment is a method executable by an apparatus configured to calculate a risk assessment value of an event sequence which is a partially ordered set indicating some events of an event group of M kinds of events (M is a finite natural number) in a time series, the method including converting the partially ordered set into an approximate totally ordered set; and on the basis of the totally ordered set obtained by the conversion, calculating a positive semi-definite matrix that minimizes a calculation error of a label value indicating whether or not a risk occurs, and calculating a projection matrix for calculating the risk assessment value on the basis of the calculated positive semi-definite matrix.

Moreover, in order to achieve the forgoing objective, an apparatus according to a fifth embodiment is an apparatus configured to calculate a risk assessment value of an event sequence which is a partially ordered set indicating some events of an event group of M kinds of events (M is a finite natural number) in a time series, the apparatus including: a converter configured to convert the partially ordered set into an approximate totally ordered set; a feature vector calculator configured to calculate an M-dimensional feature vector from the totally ordered set obtained by the conversion; and a projection matrix calculator configured to calculate a projection matrix for calculating the risk assessment value on the basis of the calculated M-dimensional feature vector.

In addition, in an apparatus according to a sixth embodiment, the converter in the fifth invention generates an M-dimensional sparse ordered matrix on the basis of the partially ordered set, and calculates a dense ordered matrix having highest similarity to the generated sparse ordered matrix.

Moreover, in an apparatus according to a seventh embodiment, the projection matrix calculator in the sixth invention converts the calculated dense ordered matrix into a column vector, and performs linear regression to calculate a projection matrix for calculating a label value indicating whether or not a risk occurs.

Further, a computer program according to an eighth embodiment is executable by an apparatus configured to calculate a risk assessment value of an event sequence which is a partially ordered set indicating some events of an event group of M kinds of events (M is a finite natural number) in a time series, and causes the apparatus to function as: a converter configured to convert the partially ordered set into an approximate totally ordered set; a feature vector calculator configured to calculate an M-dimensional feature vector from the totally ordered set obtained by the conversion; and a projection matrix calculator configured to calculate a projection matrix for calculating the risk assessment value, on the basis of the calculated M-dimensional feature vector.

A computer program according to a ninth embodiment causes the converter in the eighth invention to function as a unit to generate an M-dimensional sparse ordered matrix on the basis of the partially ordered set, and to calculate a dense ordered matrix having highest similarity to the generated sparse ordered matrix.

Furthermore, a computer program according to a tenth embodiment causes the projection matrix calculator in the ninth invention to function as a unit to convert the calculated dense ordered matrix into a column vector, and to perform linear regression to calculate a projection matrix for calculating a label value indicating whether or not a risk occurs.

The risk assessment value for each of event sequences different in length and elements can be calculated by converting a partially ordered set (matrix) indicating the event sequence into a totally ordered set (matrix). Thus, the risks incurred by the respective event sequences can be easily compared with each other. Moreover, since the risk assessment value for a given event sequence is calculated, the risk of a possible critical incident can be objectively assessed.

Hereinafter, risk calculators for calculating a risk assessment value for an event sequence according to embodiments of the present invention will be described on the basis of the drawings. More specifically, the risk calculator calculates the risk assessment value that indicates a risk of the occurrence of a certain incident for each event sequence including some of events that occur in a time series. As a matter of course, the following embodiments are not intended to limit the invention described in the scope of claims, and the entire combination of characteristic matters described in the embodiments is not necessarily essential to the solving means of the invention.

Moreover, the present invention embodiments can be implemented in a variety of different embodiments, and should not be interpreted by being limited to the description in the embodiments. Throughout the embodiments, the same reference signs are assigned to the same components.

In the following embodiments, description will be provided for an apparatus constructed by installing a computer program into a computer system. However, as is apparent to those skilled in the art, part of the present invention can be implemented as a computer-implementable computer program. Hence, the present invention can be implemented in any one of a hardware embodiment, a software embodiment, or an embodiment of a combination of hardware and software, as a risk calculator capable of calculating a risk in an event sequence including part of events by calculating a totally ordered set on the basis of an ordered set of the event sequence, and by calculating a risk assessment value for the event sequence. The computer program may be stored in any computer-readable storage medium such as a hard disk, a DVD, a CD, an optical storage device, and a magnetic storage device.

According to the embodiments of the present invention, the risk assessment value for each of event sequences different in length and elements can be calculated by converting the partially ordered set (matrix) indicating the event sequence into the totally ordered set (matrix). Accordingly, the risks incurred by the respective event sequences can be easily compared with each other. Moreover, since the risk assessment value for a given event sequence is calculated, the risk for a possible critical incident can be objectively assessed.

FIG. 1 is a block diagram schematically illustrating a configuration of a risk calculator according to a first embodiment of the present invention. The risk calculator 1 according to the first embodiment of the present invention includes at least a CPU (central processing unit) 11, a memory 12, a storage device 13, an I/O interface 14, a video interface 15, a portable disk drive 16, a communication interface 17 and an internal bus 18 that connects the foregoing hardware components together.

The CPU 11 is connected to the foregoing hardware components through the internal bus 18 and controls operations of the foregoing hardware components. In addition, the CPU 11 executes various software functions according to a computer program 100 stored in the storage device 13. The memory 12 includes a volatile memory such as a SRAM or a SDRAM. In the memory 12, a load module of the computer program 100 is loaded during the running of the computer program 100 and temporary data and the like generated during the running of the computer program 100 are stored.

The storage device 13 includes a built-in and fixed storage device (hard disk), ROM or the like. The computer program 100 is stored in the storage device 13 by being downloaded by the portable disk drive 16 from a portable storage medium 90 such as a DVD or a CD-ROM in which information such as programs and data is stored. In the run time, the computer program 100 stored in the storage device 13 is loaded from the storage device 13 to the memory 12 and then is executed. As a matter of course, the computer program 100 may be a computer program downloaded from an external computer connected to the risk calculator 1 via the communication interface 17.

The communication interface 17 is connected to the internal bus 18. By being connected to an external network such as the Internet, LAN, or WAN, the communication interface 17 enables data transmission and reception to and from an external computer and the like.

The I/O interface 14 is connected to input devices such as a keyboard 21 and a mouse 22, and receives input of data. The video interface 15 is connected to a display device 23 such as a CRT display or a liquid crystal display, and displays predetermined images on the display device 23.

Figure 2:
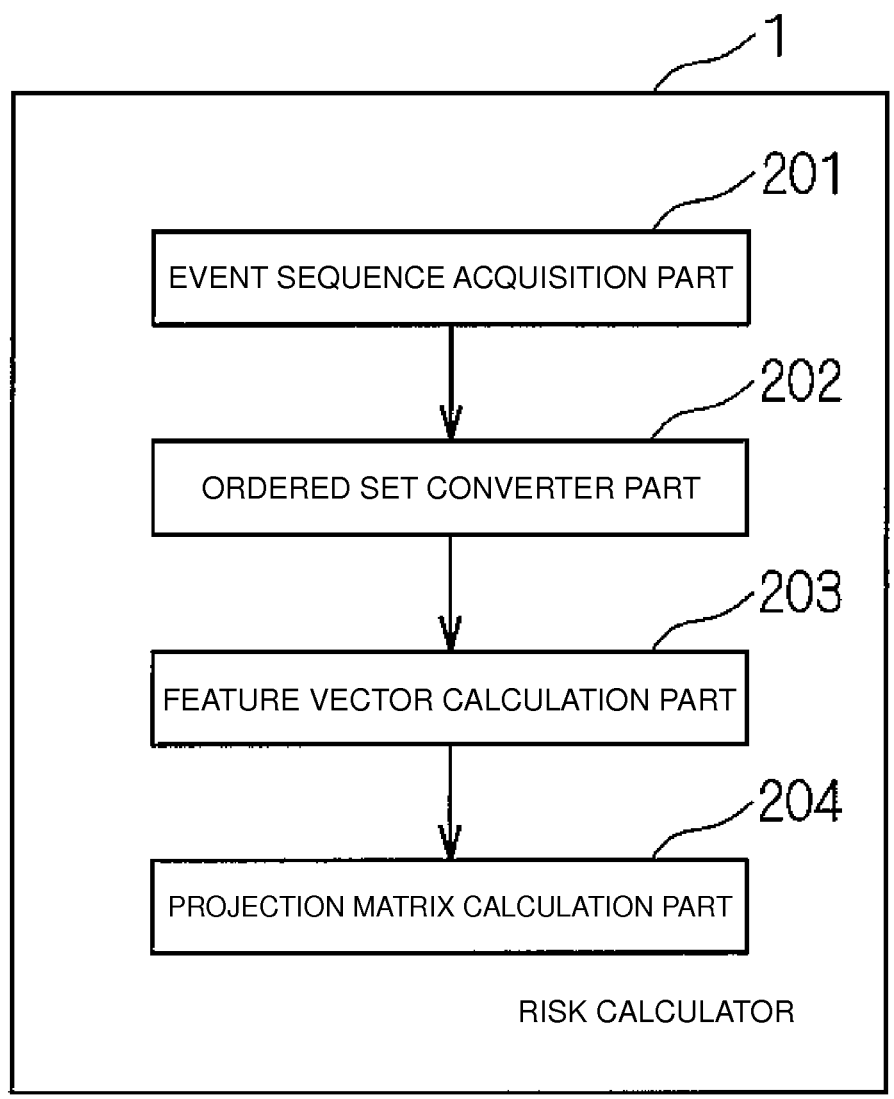
FIG. 2 is a functional block diagram of the risk calculator according to the first exemplary embodiment of the present invention.

FIG. 2 is a functional block diagram of the risk calculator 1 according to the first embodiment of the present invention. In FIG. 2, an event sequence acquisition part 201 of the risk calculator 1 acquires, as training data, event sequences each of which is time-series data of multiple events. To be more specific, the event sequence acquisition part 201 acquires a finite number N of event sequences (N is a natural number), a risk value of each of the event sequences, and similarities among elements in each of the event sequences.

FIG. 3 is a diagram illustrating event sequences acquired by the risk calculator 1 according to the first embodiment of the present invention. In the example of FIG. 3, event sequences consisting of a finite number of M kinds of events are expressed as event sequences 1, 2, . . . , i, j, . . . , N, and the event sequence 1, for example, is shown as a sequence in which events A, B, C, E, F occur in this order. The values "1.0" and "0.0" in the right column are shown as label values indicating whether or not a risk occurs. Each event sequence is assigned the label value "1.0" or "0.0" where the label value "1.0" indicates that a risk occurs and the label value "0.0" indicates that a risk does not occur.

FIG. 4 is an illustration of a similarity matrix S indicating similarities among events included in each of the event sequences. The similarity between an event i and an event j, for example, can be expressed as an element Sij in the i-th row and the j-th column of the similarity matrix S. Here, a similarity matrix is obtained in which the similarity between the same events is expressed as "1" and a value closer to "1" is assigned to an element for events having a higher similarity.

Incidentally, the event sequences may be acquired from an external computer connected via the communication interface 17, or may be acquired by being downloaded by the portable disk drive 16 from the portable storage medium 90 such as a DVD or a CD-ROM. Instead, the event sequences may be directly inputted to the risk calculator 1 via the input devices such as the keyboard 21 and the mouse 11.

Returning to FIG. 2, an ordered set converter part (converter) 202 generates a partially ordered matrix (partially ordered set) indicating an ordering of events on the basis of each of the acquired event sequences, and converts the generated partially ordered matrix to an approximate totally ordered matrix (totally ordered set). To be more specific, since an acquired event sequence does not include all conceivable kinds of events, the partially ordered matrix is converted into the totally ordered matrix through interpolation of elements including no events in the partially ordered matrix.

FIG. 5 is an illustration of a partially ordered matrix generated by the risk calculator 1 according to the first embodiment of the present invention. FIG. 5 illustrates, as the partially ordered matrix of the event sequence 1 in FIG. 3, a partially ordered matrix $X^{(1)}$ on the assumption that there are seven kinds of events A to G.

As shown in FIG. 5, the rows from the top correspond to the events A, B, . . . , G, respectively, whereas the columns from the left correspond to the events A, B, . . . , G, respectively. Here, $\beta$ is a preset value smaller than 1, and is used to assign an event a value depending on its distance from the event of each row.

In the event sequence 1 shown in FIG. 3, for example, the events A, B, C, E, and F occur. When viewed from the event A (in the first row), the event B has a distance of '1' and thus has its element determined as "$\beta$," the event C has a distance of '2' and thus has its element determined as "$\beta^2$," and the event D is not present and thus has its element determined as "0."

In summary, an element $X^{(i)}(e1, e2)$ in a partially ordered matrix $X^{(i)}$ of an event sequence i can be obtained in accordance with (Formula 1). In (Formula 1), a function I(e1, e2) is a function of returning '1' if an event e1 precedes an event e2, and returning '0' if otherwise. Then, s denotes the number of hops (a value proportional to the distance between the two). For example, the number of hops is '1' in the case of the event B from the event A, and is '2' in the case of the event C from the event A. In this way, a partially ordered matrix can be generated in which the element of an event takes a smaller value as the event becomes farther from a reference event.

$$X^{(i)}_{e1,e1} = I(e1,e2)\beta^S \quad \text{Formula 1}$$

Although a partially ordered matrix based on Formula 1 is generated for each event sequence, the generated matrix is a sparse ordered matrix in which most of the elements are 0. For this reason, interpolation on the partially ordered matrixes is performed using a so-called label propagation method. Specifically, in accordance with Formula 2, a dense ordered matrix U is calculated in which the elements in the partially ordered matrix are interpolated so that the similarities among the events can be minimized.

$$U = \operatorname{argmin}_{\{U^{(1)}, U^{(2)}, \ldots, U^{(N)}\}} \sum_{k=1}^{N} \|X^{(k)} - U^{(k)}\|_2^2 + \quad \text{Formula 2}$$

$$\lambda \sum_{k=1}^{N} \sum_{i1,i2,j1,j2} \tilde{S}_{(i1,j1),(i2,j2)} \left( U^{(k)}_{(i1,j1)} - U^{(k)}_{(i2,j2)} \right)^2$$

Returning to FIG. 2, a feature vector calculation part 203 calculates an M-dimensional feature vector from the totally ordered matrix (totally ordered set) obtained by the conversion. To be more specific, the totally ordered matrix is converted to a column vector with a single column. For example, a function vec of converting a 3-by-3 matrix to a column vector is defined as shown in Formula 3.

$$vec\left(\begin{pmatrix} a & b & c \\ d & e & f \\ g & h & i \end{pmatrix}\right) = \begin{pmatrix} a \\ b \\ c \\ d \\ e \\ f \\ g \\ h \\ i \end{pmatrix} \quad \text{Formula 3}$$

Returning to FIG. 2, a projection matrix calculation part 204 calculates a projection matrix for calculating a risk assessment value, on the basis of the calculated M-dimensional feature vector. To be more specific, the projection matrix calculation part 204 converts the calculated M-dimensional ordered matrixes $U^{(i)}$(i=1 to N) to N column vectors, respectively, in accordance with Formula 3, and performs linear regression to calculate a projection matrix A and an error b which are for calculating a risk assessment value from an event sequence.

That is to say, this is just a calculation of obtaining the projection matrix A and the error b through linear regression in a case where a relationship between a risk value (label value) $y^{(i)}$(i=1 to N) obtained when a vector sequence is acquired, and its corresponding vector sequence $U^{(i)}$(i=1 to N) is defined as shown in Formula 4.

$$f(U) = A \cdot vec(U) + b \quad \text{Formula 4}$$

The projection matrix A and the error b in Formula 4 can be obtained in the steps of expanding an equation in Formula 4 into equations as shown in Formula 5 and solving the equation using L1 normalization or L2 normalization. When the projection matrix A and the error b are determined, a risk value $y^{(i)}$(i=1 to N)=f(U) for input of any vector sequence $U^{(i)}$(i=1 to N) can be calculated as a risk assessment value.

$$y^{(1)} = A \cdot vec(U^{(1)}) + b \quad \text{Formula 5}$$

$$y^{(2)} = A \cdot vec(U^{(2)}) + b$$

$$\ldots$$

$$y^{(M)} = A \cdot vec(U^{(M)}) + b$$

Figure 6:
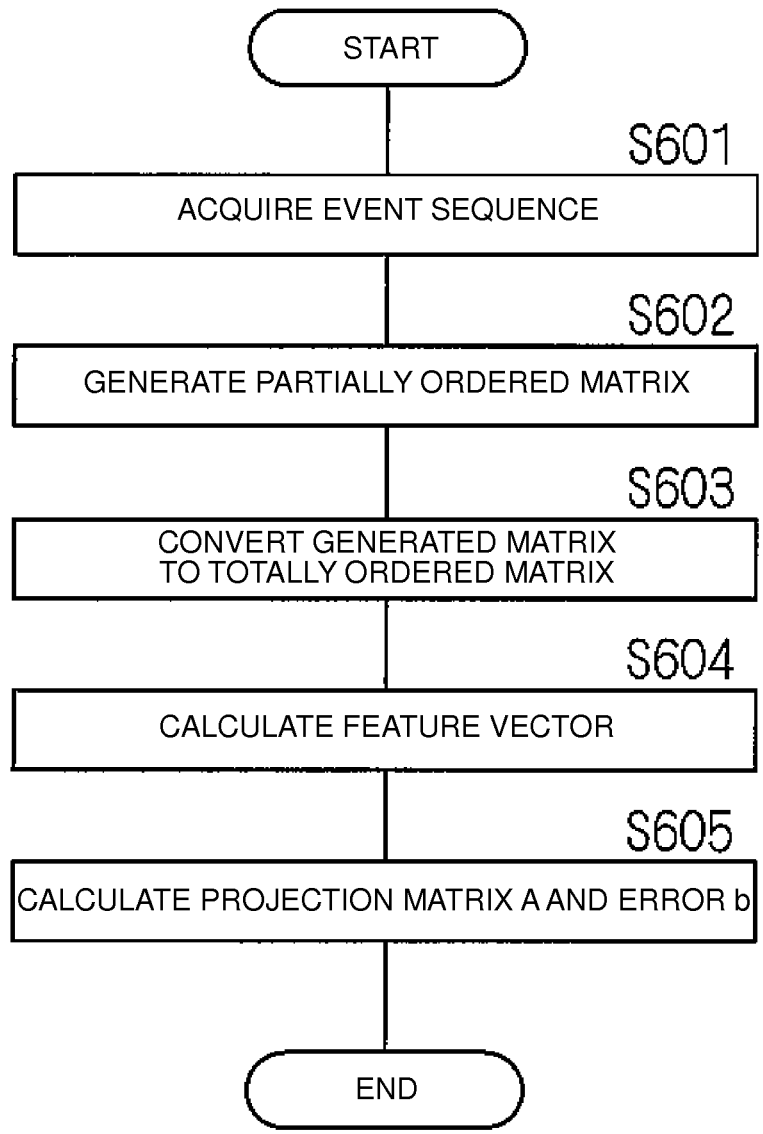
FIG. 6 is a flowchart a processing procedure of a CPU the risk calculator according to the first exemplary embodiment of the present invention.

FIG. 6 is a flowchart showing a processing procedure of the CPU 11 of the risk calculator 1 according to the first embodiment of the present invention. The CPU 11 of the risk calculator 1 acquires event sequences each of which is time-series data of multiple events (step S601). More specifically, the CPU 11 calculates a finite number N of event sequences (N is a natural number), a risk value of each of the event sequences, and similarities among elements included in each of the event sequences.

The CPU 11 generates a partially ordered matrix (partially ordered set) indicating the ordering of events on the basis of each of the acquired event sequences (S602), and converts the generated partially ordered matrix into an approximate totally ordered matrix (totally ordered set) (S603). Specifically, since each of the acquired event sequences does not include all conceivable kinds of events, the partially ordered matrix is converted into the totally ordered matrix through interpolation of elements including no events in the partially ordered matrix.

The CPU 11 calculates an M-dimensional feature vector (column vector) from the totally ordered matrix (S604) obtained by the conversion. Specifically, the totally ordered matrix is converted into the column vector with a single column.

The CPU 11 performs linear regression based on the calculated M-dimensional feature vector (column vector) to calculate the projection matrix A and the error b to be used to calculate a risk assessment value from the event sequence. By use of these values, the risk assessment value for input of a given vector sequence can be calculated in accordance with Formula 4.

According to the first embodiment as described above, the risk assessment value for each of event sequences different in length and elements can be calculated by converting the partially ordered set (matrix) indicating the event sequence into the totally ordered set (matrix). Accordingly, the risks incurred by the respective event sequences can be easily compared with each other. Moreover, since the risk assessment value for a given event sequence is calculated, the risk of a possible critical incident can be objectively assessed.

A configuration of a risk calculator according to a second embodiment is the same as that in the first embodiment, and hence the detailed description thereof is omitted herein with the same reference signs assigned to the components. The second embodiment is different from the first embodiment in that the second embodiment calculates the risk assessment value without using the feature vector.

Figure 7:
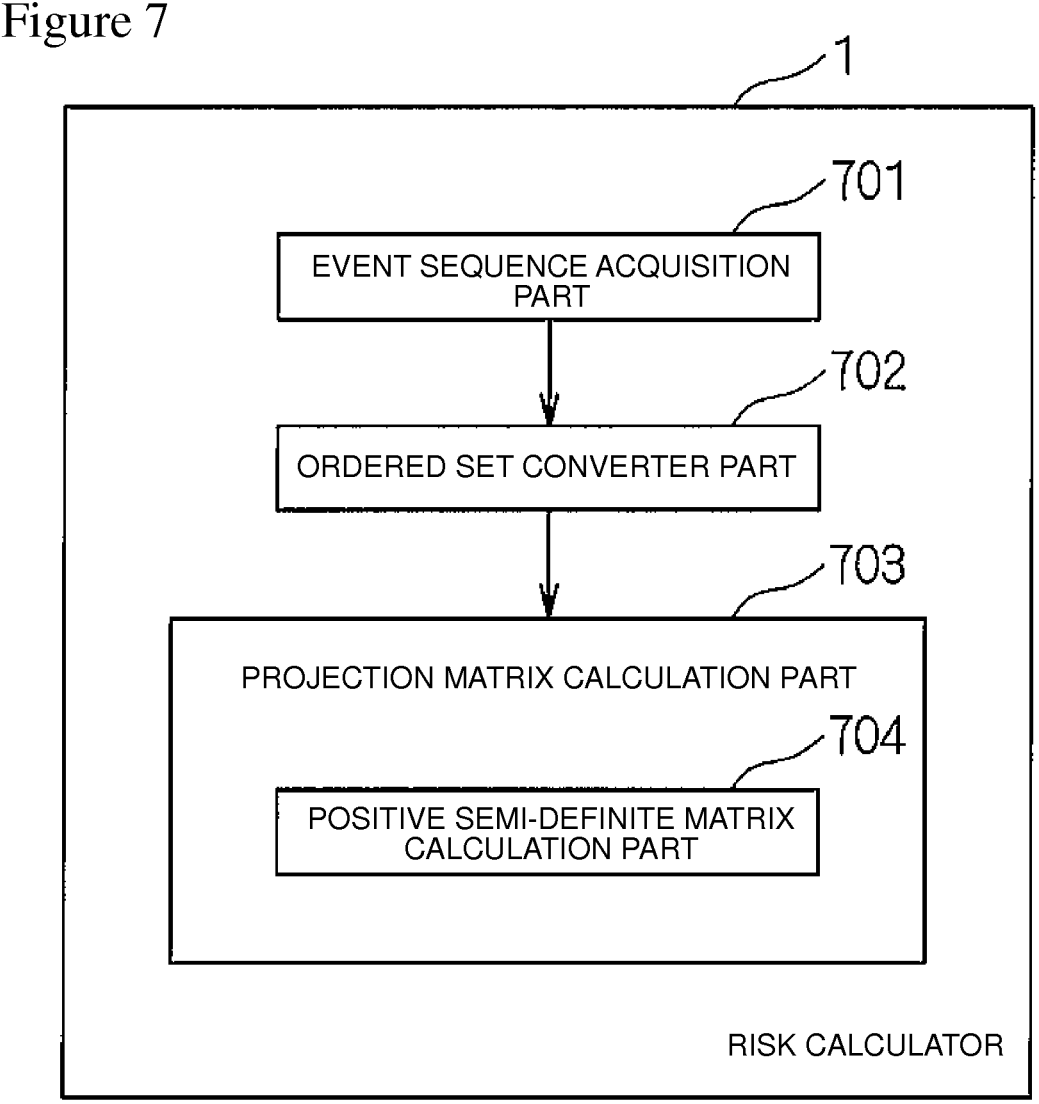
FIG. 7 is a functional block diagram of a risk calculator according to a second exemplary embodiment of the present invention.

FIG. 7 is a functional block diagram of a risk calculator 1 according to the second embodiment of the present invention. In FIG. 7, an event sequence acquisition part 701 of the risk calculator 1 acquires, as training data, event sequences each of which is time-series data of multiple events. To be more specific, the event sequence acquisition part 701 acquires a finite number N of event sequence (N is a natural number), a risk value for each of the event sequences and similarities among elements included in each of the event sequences.

The event sequences may be acquired from an external computer connected via the communication interface 17, or may be acquired by being downloaded by the portable disk drive 16 from the portable storage medium 90 such as a DVD or a CD-ROM. Instead, the event sequences may be directly inputted to the risk calculator 1 via the input devices such as the keyboard 21 and the mouse 11.

An ordered set converter part (converter) 702 generates a partially ordered matrix (partially ordered set) indicating an ordering of events on the basis of each of the acquired event sequences, and converts the generated partially ordered matrix to an approximate totally ordered matrix (totally ordered set). To be more specific, since an acquired event sequence does not include all conceivable kinds of events, the partially ordered matrix is converted into the totally ordered matrix through interpolation of elements including no events in the partially ordered matrix.

A projection matrix calculation part 703 includes a positive semi-definite matrix calculation part 704. The positive semi-definite matrix calculation part 704 calculates a positive semi-definite matrix such that a calculation error of a label value indicating whether or not a risk occurs can be minimized, on the basis of the totally ordered matrix (totally ordered set) obtained by the conversion. Here, the positive semi-definite matrix is a matrix in which eigenvalues are 0 or positive.

To be more specific, when V denotes a positive semi-definite matrix to be calculated, and $\epsilon$ denotes a calculation error, the matrix that minimizes the calculation error $\epsilon$ is the positive semi-definite matrix V. Hence, it is only necessary to calculate the positive semi-definite matrix V satisfying Formula 6.

$$\min_{V,\epsilon>0} \epsilon$$

$$s.t. Tr(VU^{(i+)}) \geq y^{(i+)} - \epsilon$$

$$Tr(VU^{(i-)}) \leq y^{(i-)} + \epsilon \quad \text{Formula 6}$$

In Formula 6, "Tr" denotes a function of adding up diagonal elements in a matrix, and returning a scalar value that is the sum of the diagonal elements. In the case where the label value of the (i+)-th time series is '1,' that is, where a risk occurs, the positive semi-definite matrix V satisfying Formula 6 is calculated as shown in the second line of Formula 6. On the other hand, in the case where the label value of the (i−)-th time series is '0,' that is, where no risk occurs, the positive semi-definite matrix V satisfying Formula 6 is calculated as shown in the third line of Formula 6.

As a matter of course, the positive semi-definite matrix V may be calculated by using an approximate matrix Z (Z is also a positive semi-definite matrix). In this case, the positive semi-definite matrix V is calculated by obtaining the approximate matrix Z that minimizes a threshold (error) $\eta$ on the basis of Formula 7. Here, in Formula 7, an arithmetic operator "∘" indicates multiplication of elements in matrixes on both sides of the operator.

$$\min_{V,\epsilon>0} \eta$$

$$s.t. Z_{ii} \leq \eta \text{ for } i=1,\ldots,M$$

$$Z \circ V \geq E \quad \text{Formula 7}$$

The calculated positive semi-definite matrix V is equivalent to the projection matrix A. Thus, for input of a given vector sequence, the risk assessment value can be calculated by using Formula 4.

Figure 8:
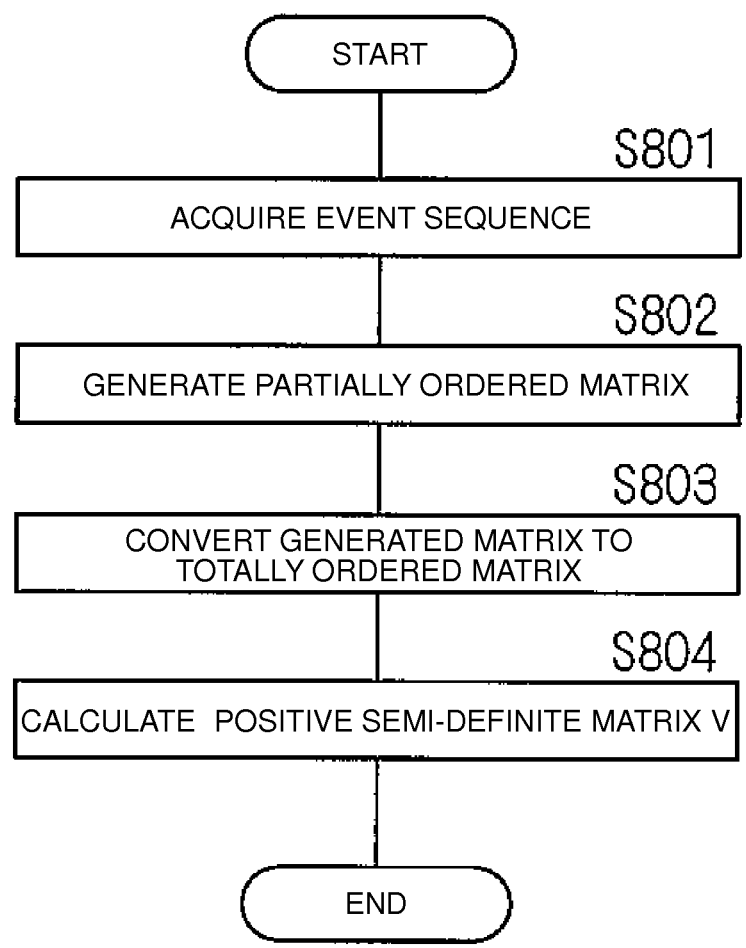
FIG. 8 is a flowchart a processing procedure of a CPU the risk calculator according to the second exemplary embodiment of the present invention.

FIG. 8 is a flowchart showing a processing procedure of the CPU 11 of the risk calculator 1 according to Embodiment 2 of the present invention. The CPU 11 of the risk calculator 1 acquires event sequences each of which is time-series data of multiple events (S801). More specifically, the CPU 11 calculates a finite number N of event sequences (N is a natural number), a risk value of each of the event sequences, and similarities among elements included in each of the event sequences.

The CPU 11 generates a partially ordered matrix (partially ordered set) indicating the ordering of events on the basis of each of the acquired event sequences (S802), and converts the generated partially ordered matrix into an approximate totally ordered matrix (totally ordered set) (S803). Specifically, since each of the acquired event sequences does not include all conceivable kinds of events, the partially ordered matrix is converted into the totally ordered matrix through interpolation of elements including no events in the partially ordered matrix.

The CPU 11 calculates the positive semi-definite matrix V that minimizes the calculation error of the label value indicating whether or not a risk occurs, on the basis of the totally ordered matrix (totally ordered set) obtained by the conversion (S804). To be more specific, when V denotes a positive semi-definite matrix to be calculated and $\epsilon$ denotes a calculation error of the label value, the matrix that minimizes the calculation error $\epsilon$ is the positive semi-definite matrix V.

According to Embodiment 2 as described above, the risk assessment value for each of event sequences different in length and elements can be calculated by converting the partially ordered matrix (set) indicating the event sequence into the totally ordered matrix (set). Accordingly, the risks incurred by the respective event sequences can be easily compared with each other. In addition, the risk assessment value for any given event sequence can be calculated without having to calculate the feature vector.

The foregoing first and second embodiments are effective when being applied to event sequences in the medical field. Since there are a wide variety of conditions of a patient such for example as a headache, a stomachache, a bellyache and sick feeling, it is difficult to judge whether or not these conditions appear as a symptom of a serious disease. In this respect, a risk of getting a serious disease such as diabetes or cancer may be reduced if either embodiment is applied to a model of collecting, as event sequences to be used as training data, data of many patients such as data on medical examination by interview and data on their daily lives, and estimating the risk of getting the serious disease.

It should be noted that the present invention is not limited to the foregoing embodiments, and can be altered and modified in various ways within the gist and scope of the present invention. It is needless to say that the present invention is not limited to event sequences in the medical field described as an example, but is applicable to any phenomenon having a cause and a result.

The invention claimed is:

1. A method of determining a risk assessment value of an event sequence which is a partially ordered set indicating some events of an event group of M kinds of events in a time series, wherein M is a finite natural number, the method comprising:
converting, with a processing device, the partially ordered set into an approximate totally ordered set;
calculating an M-dimensional feature vector from the totally ordered set obtained by the conversion; and calculating a projection matrix for calculating the risk assessment value on the basis of the calculated M-dimensional feature vector.

2. The method according to claim 1, further comprising:

generating an M-dimensional sparse ordered matrix on the basis of the partially ordered set; and calculating a dense ordered matrix having a highest similarity to the generated sparse ordered matrix.

3. The method according to claim 2, further comprising:

converting the calculated dense ordered matrix into a column vector; and calculating, with a projection matrix, a label value indicating whether or not a risk occurs by linear regression.

4. A method of determining a risk assessment value of an event sequence which is a partially ordered set indicating some events of an event group of M kinds of events in a time series, wherein M is a finite natural number, the method comprising:

converting, with a processing device, the partially ordered set into an approximate totally ordered set; and on the basis of the totally ordered set obtained by the conversion, calculating a positive semi-definite matrix that minimizes a calculation error of a label value indicating whether or not a risk occurs, and calculating a projection matrix for calculating the risk assessment value on the basis of the calculated positive semi-definite matrix.

\* \* \* \* \*